United States Patent
Sun et al.

(10) Patent No.: US 10,913,721 B2
(45) Date of Patent: Feb. 9, 2021

(54) CRYSTALLINE FORM OF ARIPIPRAZOLE

(71) Applicant: Noratech Pharmaceuticals, Inc., Taipei (TW)

(72) Inventors: Yun-Zhe Sun, Nanjing (CN); Wei-Ming Jiang, Nanjing (CN); Xin Zhao, Nanjing (CN); Cheng-Gang Lin, Nanjing (CN); Li Gui, Nanjing (CN); Fei Liu, Nanjing (CN)

(73) Assignee: NANJING NORATECH PHARMACEUTICALS CO., LTD, Nanjing (CN)

( * ) Notice: Subject to any disclaimer, the term of this patent is extended or adjusted under 35 U.S.C. 154(b) by 215 days.

(21) Appl. No.: 15/999,610

(22) PCT Filed: Feb. 19, 2016

(86) PCT No.: PCT/CN2016/074135
§ 371 (c)(1),
(2) Date: Aug. 20, 2018

(87) PCT Pub. No.: WO2017/139971
PCT Pub. Date: Aug. 24, 2017

(65) Prior Publication Data
US 2020/0071293 A1    Mar. 5, 2020

(51) Int. Cl.
*C07D 215/22* (2006.01)
*A61K 31/496* (2006.01)
*A61P 25/00* (2006.01)

(52) U.S. Cl.
CPC ............ *C07D 215/22* (2013.01); *A61P 25/00* (2018.01); *C07B 2200/13* (2013.01)

(58) Field of Classification Search
CPC .................................................... C07D 215/22
See application file for complete search history.

(56) References Cited

U.S. PATENT DOCUMENTS

| 7,491,726 B2 * | 2/2009 | Parthasaradhi ...... C07D 215/22 514/253.07 |
| 2007/0202181 A1 | 8/2007 | Bando et al. |

FOREIGN PATENT DOCUMENTS

| CN | 1463191 A | 12/2003 |
| CN | 102372672 A | 3/2012 |
| EP | 1 686 117 A1 | 8/2006 |

OTHER PUBLICATIONS

English Translation for CN 102372672 (Mar. 14, 2012) (Year: 2012).*
Saeed et al. International Journal of Engineering Research & Technology (IJERT) vol. 5 Issue 01, p. 405-412. (Year: 2016).*
International Search Report for PCT/CN2016/074135 (PCT/ISA/210) dated Apr. 20, 2016.

* cited by examiner

*Primary Examiner* — Emily A Bernhardt
(74) *Attorney, Agent, or Firm* — Birch, Stewart, Kolasch & Birch, LLP

(57) ABSTRACT

The present invention relates to a crystalline form N of aripiprazole, pharmaceutical compositions thereof and the use of crystalline form N in the preparation of a medicament for the treatment of central nervous system diseases, especially schizophrenia.

7 Claims, 3 Drawing Sheets

Created using NETZSCH Proteus Software

CRYSTALLINE FORM OF ARIPIPRAZOLE

FIELD OF THE INVENTION

The present invention relates to a new crystalline form N of aripiprazole, a pharmaceutical composition thereof and the use of the crystalline form N in the preparation of a medicament for the treatment of central nervous system diseases, especially schizophrenia.

BACKGROUND OF THE INVENTION

Aripiprazole, which has the chemical name 7-{4-[4-(2,3-dichlorophenyl)-1-piperazinyl]-butoxy}-3,4-dihydroquinolone, is an atypical psychotic drug for the treatment of schizophrenia. This drug is sold under the tradename Abilify in various areas including China, the United States, Europe, etc.

Aripiprazole is a polymorphous substance, and the crystalline form thereof is diversified by changes in the crystallization solvent, the crystallization method, the drying method, etc. WO 03/026659 discloses the type-I crystals and the type-II crystals stated in the 4th Japanese-Korean Symposium on Separation Technology (October 6-8, 1996), which states that the type-I crystals can be prepared by crystallization in an ethanol solution, or by heating a hydrate of aripiprazole at 80° C., and the aripiprazole crystals prepared thereby possess significant hygroscopicity; and the type-II crystals can be prepared by heating the type-I crystals at 130° C. to 140° C. for 15 hours; however, by means of the aforementioned methods. The type-II crystals having a high purity cannot be easily prepared on an industrial scale with good repeatability. This patent further discloses 7 crystalline forms of the hydrates, i.e., type-A, type-B, type-C, type-D, type-E, type-F, and type-G. It can be seen from the description that in order to obtain these disclosed crystalline forms, the type-I crystals are firstly prepared; and then the type-I crystals of aripiprazole are placed at a relatively high temperature and heated for a long time, or are dispersed in an organic solvent and subjected to a heating treatment for a long time. Although the crystalline forms of aripiprazole prepared thereby possess a low hygroscopicity, the process is complicated and involves significant costs, which is not conducive to large-scale industrial production. CN 1760183 discloses two crystalline forms, i.e., crystalline form α and crystalline form β, wherein crystalline form α is a ½ ethanol solvate of aripiprazole, has certain limitations in terms of the drying, processing and formulation processes, and is not suitable for pharmaceutical formulation; furthermore, crystalline form β is prepared under specific conditions after firstly preparing crystalline form α, which process is also not suitable for large-scale industrial production. It can be seen that the crystalline form of aripiprazole is greatly influenced by the preparation conditions, and any change in the conditions will result in a crystalline form with different properties. Different crystalline forms have different dissolution rates. In term of formulation, crystals with faster dissolution rates are suitable for the preparation of immediate release forms, and those with slower dissolution rates are suitable for the preparation of sustained release forms.

It is well known in the art that hydrates generally have a lower water solubility than the anhydrous form, which may be advantageous for the development of controlled or sustained release pharmaceutical preparations. Currently, there are two known aripiprazole hydrates, i.e., the conventional hydrate and hydrate A, both of which are reported in WO 03/026659.

In the treatment of schizophrenia, the immediate release preparations of aripiprazole can quickly exert its efficacy and relieve symptoms, and the long-acting sustained release preparations of aripiprazole can significantly reduce the frequency of drug administration and increase patient compliance. In order to satisfy the release requirements and be convenient for patients to use. The present invention provides a new crystalline form of aripiprazole, i.e. crystalline form N. Crystalline form N not only has a stable preparation process, but also has a slower dissolution rate than the known two aripiprazole hydrates, and as such is more suitable for use in aripiprazole sustained release preparations.

SUMMARY OF THE INVENTION

The purpose of the present invention is to provide a new crystalline form of aripiprazole, which is known as crystalline form N.

Another object of the present invention is to provide a pharmaceutical composition of crystalline form N of aripiprazole.

Crystalline form N of aripiprazole provided by the present invention is characterized in that at a heating rate of 5° C./min, the crystalline form has endothermic peaks near 125° C. and near 134° C. during differential scanning calorimetry.

In one embodiment, crystalline form N of aripiprazole has a powder X-ray diffraction pattern that is substantially the same as the powder X-ray diffraction pattern as shown in FIG. 1 in terms of peak positions.

In another embodiment, crystal form N of aripiprazole has a powder X-ray diffraction pattern substantially the same as the powder X-ray diffraction pattern as shown in FIG. 1.

In one embodiment, at a heating rate of 5° C./min, crystalline form N has an endothermic curve of differential thermal analysis that is substantially the same as the endothermic curve as shown in FIG. 2.

In one embodiment, at a heating rate of 5° C./min, the crystalline form has endothermic peaks at 124° C.-126° C. and at 133° C.-135° C. during differential scanning calorimetry.

In some embodiments, at a heating rate of 5° C./min, the crystalline form neither has an endothermic peak near 71° C. nor near 75° C. during differential scanning calorimetry. In one embodiment, at a heating rate of 5° C./min, the crystalline form neither has an endothermic peak at 70° C.-72° C. nor at 74° C.-76° C. during differential scanning calorimetry.

In one embodiment, the crystalline form also has the following property: an X-ray powder diffraction pattern having peaks expressed in degrees 2θ at 12.6±0.1, 15.1±0.1, 17.4±0.1, 18.2±0.1, 18.7±0.1, 22.5±0.1, 23.2±0.1, 24.8±0.1, and 27.5±0.1 by using a Cu-Ka radiation.

In one embodiment, crystalline form N of aripiprazole is an aripiprazole hydrate.

The present invention provides a pharmaceutical composition comprising a therapeutically effective amount of crystalline form N of aripiprazole in the present invention mixed with a pharmaceutically acceptable carrier. The pharmaceutical composition may be administered gastrointestinally or parenterally, and may be administered to a patient in the form of tablets, capsules, solutions, suspensions, etc.

The present invention describes the feature "powder X-ray diffraction pattern that is substantially the same as . . . in terms of peak positions", wherein "the same as . . . in terms of peak positions" means that the positions of the peaks expressed in degrees 2θ in the powder X-ray diffraction pattern are substantially the same. It should be noted that due to a variety of factors, some measurement errors sometimes occur in 2θ angles in the X-ray powder diffraction pattern, and the measured values will usually vary by ±0.3, preferably ±0.2, and more preferably ±0.1. Therefore, in the present description, the 2θ angle, which is based on the measured value of a specific sample, should be understood to include these permissible errors.

In the present invention, the feature "the same as the powder X-ray diffraction pattern" means that the peak positions expressed in degrees 2θ are substantially the same, and the relative intensity of the peak positions are substantially the same, wherein the relative intensity refers to, when the intensity of the peak with the highest intensity among all the diffraction peaks of the powder X-ray diffraction pattern is regarded as being 100%, the ratio of the intensity of another peak to the intensity of the peak with the highest intensity.

In the present invention, "substantially the same as the powder X-ray diffraction pattern as shown in FIG. 1" means at least 50%, or at least 60%, or at least 70%, or at least 80%, or at least 90%, or at least 95%, or at least 99% of the peaks in the powder X-ray diffraction pattern appear in the given powder X-ray diffraction pattern.

It should be noted that the absorption peak in the differential scanning calorimetric analysis is an inherent physical property of crystalline form N of the present invention. However, during actual measurement, in addition to measurement errors, the melting point may sometimes be changed due to a tolerable amount of impurities, and this possibility cannot be denied. Therefore, a person skilled in the art can fully understand to what extent the measured value of the endothermic peak temperature in the present invention can vary. For example, it is envisaged that the error is about ±5° C. in some cases, preferably about ±3° C., more preferably about ±2° C., and most preferably about ±1° C. The analysis methods used in the present invention are as follows:

1) X-Ray Powder Diffraction

A Bruker D8 advance diffractometer is used, as well as a Cu Kα fill tube (40 kV, 40 mA) at room temperature as an X-ray source with a wide angle goniometer, a 0.6 mm divergence slit, a 2.5° primary Soller slit, a 2.5° secondary Soller slit, an 8 mm anti-scatter slit, a 0.1 mm detector slit, and a LynxEye detector. In the 2θ continuous scan mode, data acquisition is completed with a scanning step of 0.02° at a scanning speed of 2.4°/min in the range of 3°-40°.

2) Differential Scanning Calorimetry

The differential thermal analysis is completed by using NETZSCH 200F3. 3 to 5 mg of a sample in placed in an aluminum plate for pressing. A blank aluminum crucible is set as a reference. Scanning is performed from room temperature to 180° C. at a heating rate of 5° C./min under a high purity nitrogen atmosphere with a flow rate of 40 mL/min.

DETAILED DESCRIPTION OF THE INVENTION

The present invention will be further described with reference to the following examples, such that the present invention will be more comprehensively understood by a person skilled in the art, and these examples are not intend to limit the present invention in any way.

Example 1

Preparation Method of Crystalline form N 2 kg of aripiprazole an hydrate is added to a 60 L acetone-water (4:1 (V/V)) system, and the temperature is raised to 70° C. Stirring is stopped until the system is completely cleared. Crystals are precipitated by naturally cooling to room temperature, and same are filtered to obtain white needle crystals for air blast drying at 40° C. until the moisture content of the material is between 3.9% and 4.4%, which crystals are 1.9 kg by weight, and the yield is 91%.

Example 2

Solid State Characterization of Crystalline Form N

The new crystalline forms are characterized as being in a solid state by X-ray powder diffraction and differential scanning calorimetry, and the solid state characterization parameters and patterns thereof are as described herein.

Comparison Example 1

Figure 3:
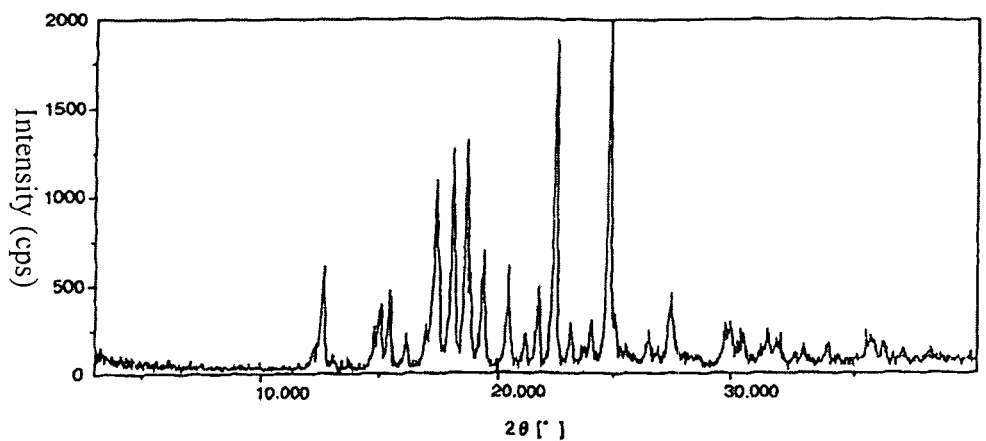
FIG. 3 is the powder X-ray diffraction pattern of hydrate A prepared according to the method in WO 03/026659.
Figure 4:
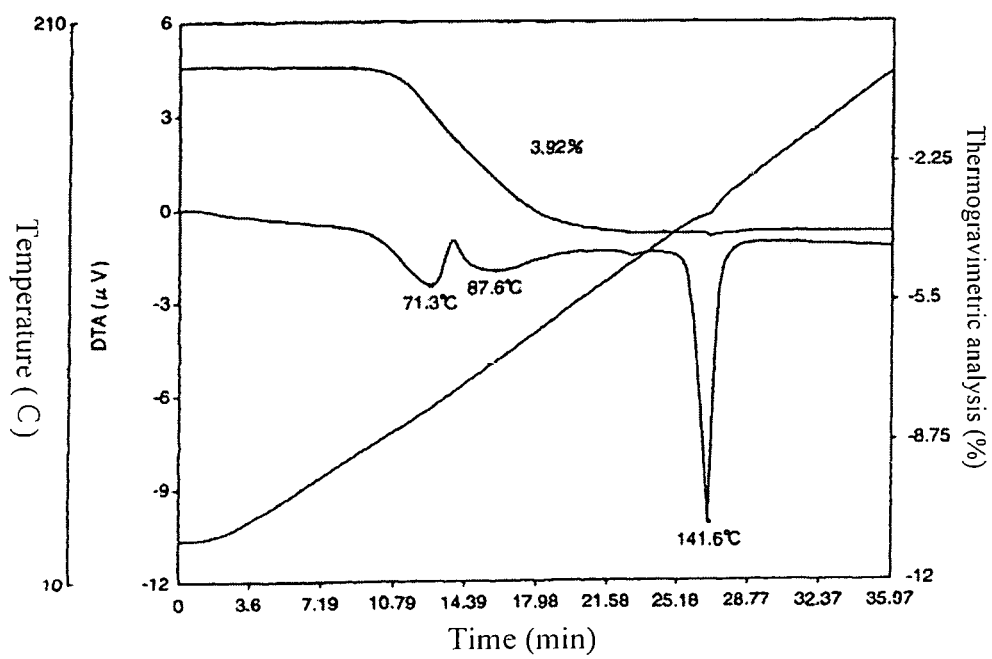
FIG. 4 is the differential thermal analysis pattern of hydrate A prepared according to the method in WO 03/026659.

Preparation Method and Solid-State Characterization of Hydrate A of Aripiprazole Hydrate A of aripiprazole is prepared according to the method in example 1 of WO 03/026659. Hydrate A is characterized as being in a solid state by X-ray powder diffraction and differential scanning calorimetry in WO 03/026659, and the solid state characterization parameters and patterns thereof are as described in WO 03/026659 (see FIG. 3 and FIG. 4 for details).

Comparison Example 2

Figure 5:
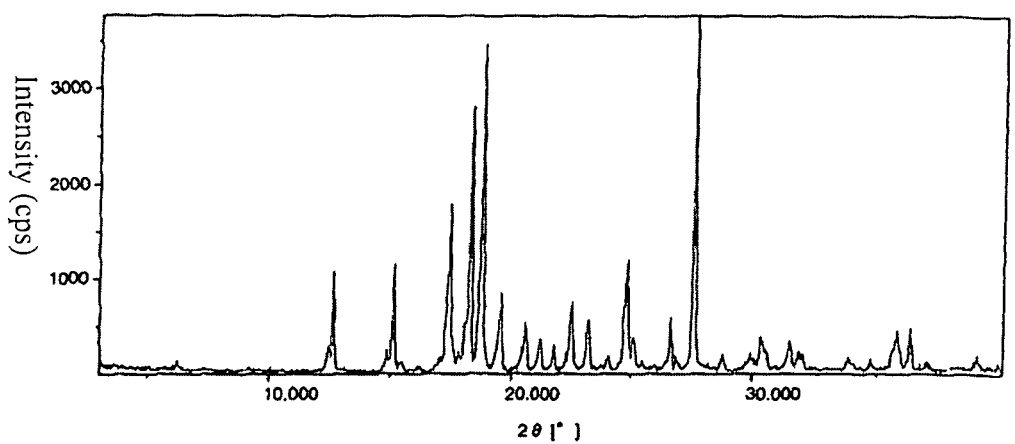
FIG. 5 is the powder X-ray diffraction pattern of the conventional hydrate prepared according to the method in WO 03/026659.
Figure 6:
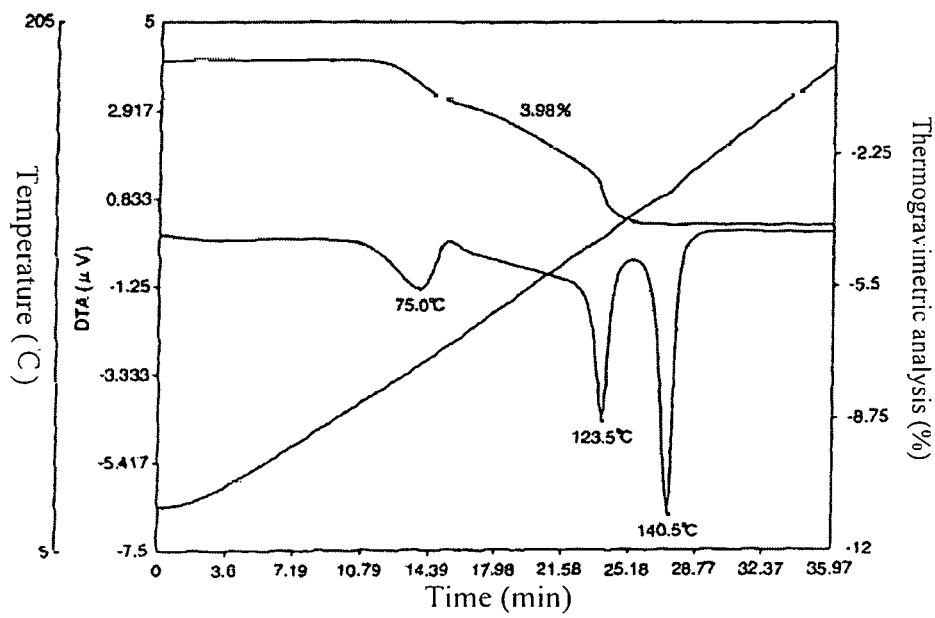
FIG. 6 is the differential thermal analysis pattern of the conventional hydrate prepared according to the method in WO 03/026659.

Preparation Method and Solid-State Characterization of Conventional Hydrate of Aripiprazole The conventional hydrate of aripiprazole is prepared according to the method in reference example 3 of WO 03/026659. Hydrate B is characterized as being in a solid state by X-ray powder diffraction and differential scanning calorimetry in WO 03/026659, and the solid state characterization parameters and patterns thereof are as described in WO 03/026659 (pages 63-64, see FIG. 5 and FIG. 6 for details).

Conclusions:

Comparing the crystalline form obtained in example 1 with that obtained in comparison example 1 (see FIG. 3 and FIG. 4), the positions of the characteristic peaks in the X-ray powder diffraction pattern are different, and the peak intensities are different. The differential thermal analysis of example 1 has an endothermic peak at about 125° C. and does not show a weak peak at about 71° C.

Comparing the crystalline form obtained in example 1 with that obtained in comparison example 2 (see FIG. 5 and FIG. 6), the positions of the characteristic peaks in the X-ray powder diffraction pattern are different, and the peak intensities are different. The differential thermal analysis of example 1 neither shows a gradual dehydration endothermic peak between about 60° C. and 120° C. nor a weak peak at about 75° C.

Therefore, crystalline form N provided by the present invention is different from the known crystalline forms of aripiprazole hydrate disclosed or claimed by the existing documents.

Example 3

Comparison Test for the Dissolution Rate of Crystalline form N, Hydrate A and the Conventional Hydrate of Aripiprazole Sample preparation: Powders of crystalline form N, hydrate A and the conventional hydrate of aripiprazole are respectively sieved through a 100-mesh sieve, and the appropriate amount of sieved material (equivalent to 50 mg of aripiprazole) is taken and measured to determine the dissolution rate of each sample.

Dissolution conditions: 0.25% sodium dodecyl sulfate solution (900 mL): slurry method: 50 rpm; 37° C.±0.5° C.

Sample detection: Samples of 3 ml are respectively taken at 15, 30, 60, 90, 120, 240, and 360 min, and immediately littered through a 0.45 μm microporous membrane, 2 mL of the initial filtrate is discarded, and the drug concentration in the subsequent filtrate is measured.

Figure 7:
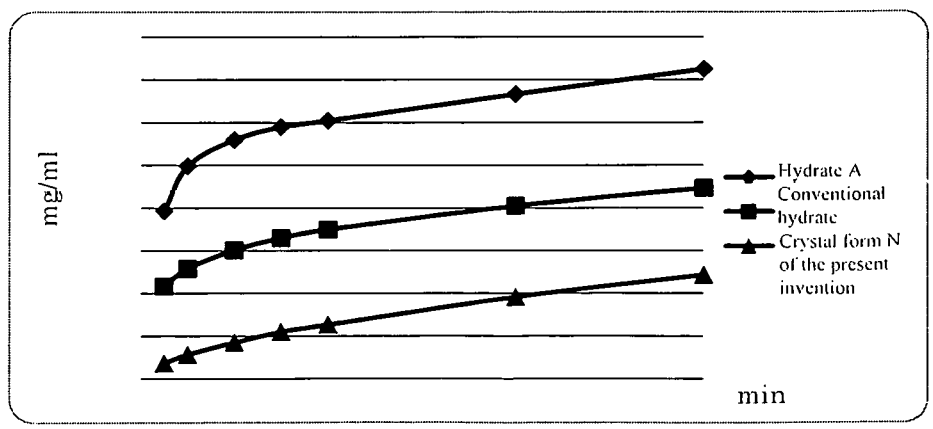
FIG. 7 is a comparison of the dissolution rates of different crystalline forms of aripiprazole.

Conclusions:

FIG. 7 shows comparison data regarding the dissolution rate of crystalline form N of the present invention, hydrate A, and the conventional hydrate. It can be seen from FIG. 7 that the dissolution rate of crystalline form N of the present invention is significantly different from that of the two known hydrates. Crystalline form N of the present invention has a slower release rate.

Example 4

Pharmaceutical Composition Comprising Crystalline Form N of Aripiprazole of the Present Invention Formula:

| Components | Formulation amount |
| --- | --- |
| Crystalline form N of aripiprazole | 400 mg (based on aripiprazole) |
| Sodium carboxymethylcellulose | 20 mg |
| Mannitol | 80 mg |
| Polyoxyethylene (20) sorbitan monooleate | 20 mg |
| Sodium dihydrogen phosphate monohydrate | 1.38 mg |
| Water for injection | Appropriate amount, adjusted to 2 mL |

Preparation Method

1) The sodium carboxymethylcellulose, mannitol, polyoxyethylene (20) sorbitan monooleate and sodium dihydrogen phosphate monohydrate are dissolved in an appropriate amount of water for injection;

2) crystalline form N of aripiprazole is added to the material obtained in step 1 and is dispersed uniformly; and 3) the water for injection is added to the material in step 2 to adjust and arrive at the target concentration, and same are then sub-packaged.

The above description merely relates to preferred embodiments of the present invention, and it should be pointed out that, for a person of ordinary skill in the art, some improvements and modifications can also be made under the premise of not departing from the principle of the present invention, and these improvements and modifications should also be considered to be within the scope of protection of the present invention.

The invention claimed is:

1. A crystalline form N of aripiprazole, wherein the crystalline form is an aripiprazole hydrate that has the following properties:
    at a heating rate of 5° C./min, the crystalline form has endothermic peaks near 125° C. and near 134° C. during differential scanning calorimetry; and
    an X-ray powder diffraction pattern having peaks expressed in degrees 2θ at 12.6±0.1, 15.1±0.1, 17.4±0.1, 18.2±0.1, 18.7±0.1, 22.5±0.1, 23.2±0.1, 24.8±0.1, and 27.5±0.1 by using a Cu-Kα radiation.

Figure 1:
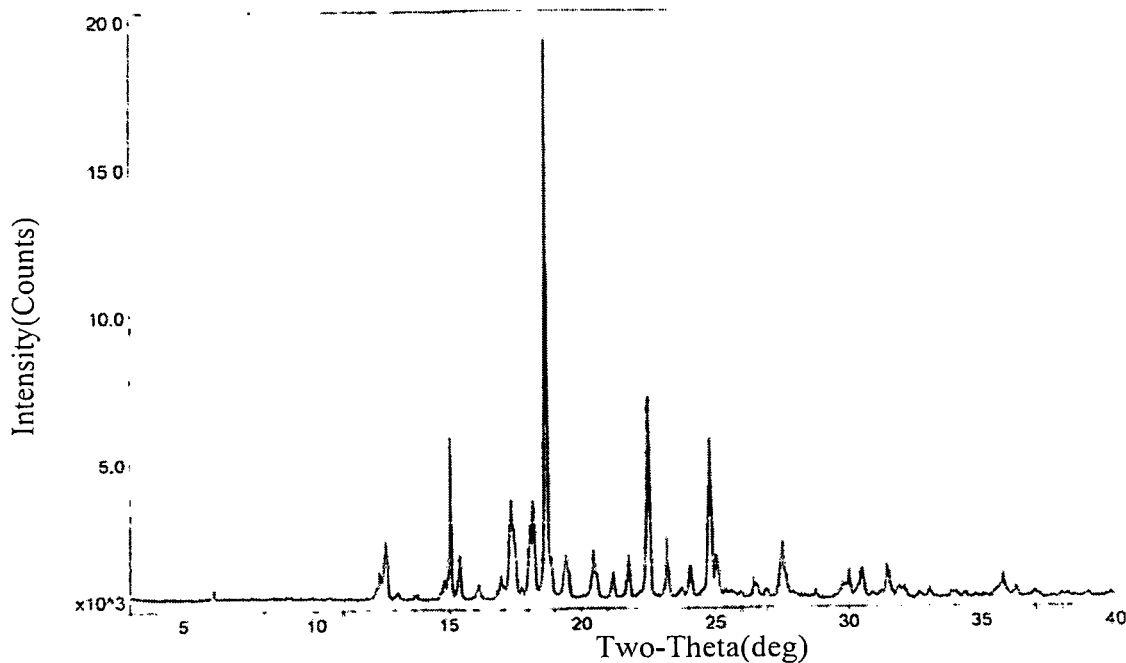
FIG. 1 is the powder X-ray diffraction pattern of crystalline form N of aripiprazole.

2. The crystalline form N of aripiprazole as claimed in claim 1, wherein the crystalline form has a powder X-ray diffraction pattern that is substantially the same as the powder X-ray diffraction pattern as shown in FIG. 1 in terms of peak positions.

Figure 2:
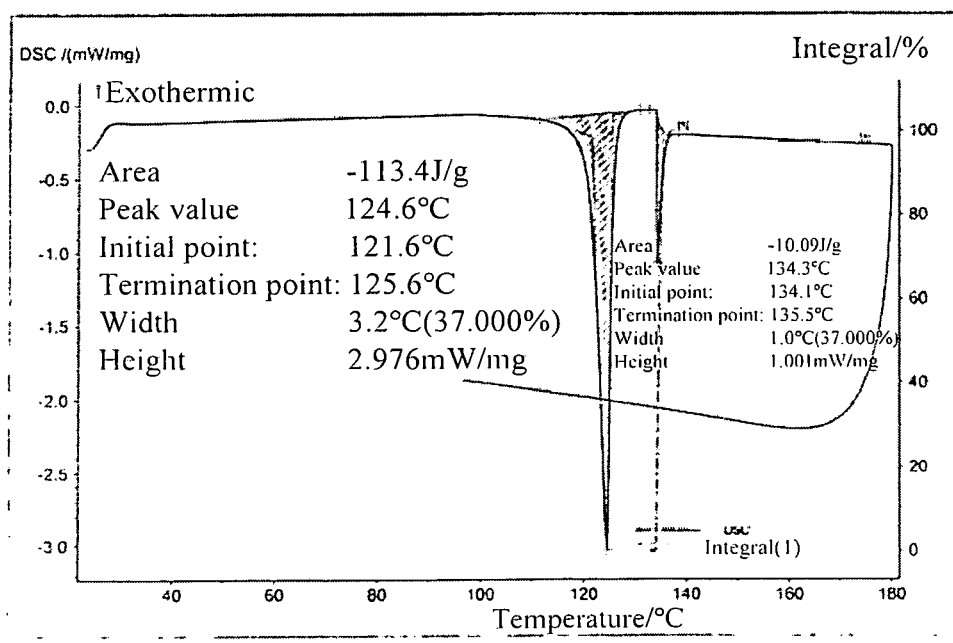
FIG. 2 is the differential thermal analysis of crystalline form N of aripiprazole.

3. The crystalline form N of aripiprazole as claimed in claim 2, wherein at a heating rate of 5° C./min, the crystalline form has an endothermic curve of differential thermal analysis that is substantially the same as the endothermic curve as shown in FIG. 2.

4. The crystalline form N of aripiprazole as claimed in claim 1, wherein at a heating rate of 5° C./min, the crystalline form has endothermic peaks at 124° C.-126° C. and at 133° C.-135° C. during differential scanning calorimetry.

5. The crystalline form N of aripiprazole as claimed in claim 1, wherein at a heating rate of 5° C./min, the crystalline form neither has an endothermic peak near 71° C. nor near 75° C. during differential scanning calorimetry.

6. The crystalline form N of aripiprazole as claimed in claim 5, wherein at a heating rate of 5° C./min, the crystalline form neither has an endothermic peak at 70° C.-72° C. nor at 74° C.-76° C. during differential scanning calorimetry.

7. A pharmaceutical composition, comprising the crystalline form N of aripiprazole according to claim 1 and a pharmaceutically acceptable carrier.

* * * * *